US00PP15579P2

(12) United States Plant Patent
Stemkens

(10) Patent No.: US PP15,579 P2
(45) Date of Patent: Feb. 22, 2005

(54) ***DIASCIA* PLANT NAMED 'DIASPETIS'**

(50) Latin Name: *Diascia barberae*
Varietal Denomination: Diaspetis

(75) Inventor: Henricus Stemkens, Hoorn (NL)

(73) Assignee: Syngenta Seeds B.V., Enkhuizen (NL)

( * ) Notice: Subject to any disclaimer, the term of this patent is extended or adjusted under 35 U.S.C. 154(b) by 84 days.

(21) Appl. No.: 10/796,683

(22) Filed: Mar. 8, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—Edouard G. Lebel

(57) ABSTRACT

A new *Diascia* plant particularly distinguished by its rosy red flowers, which produces no seeds, and has a growing habit that is spreading and hanging.

1 Drawing Sheet

Latin name of the genus and species of the plant claimed: *Diascia barberae.*
Varietal denomination: 'Diaspetis'.

BACKGROUND OF THE NEW PLANT

The present invention comprises a new distinct cultivar of *Diascia*, botanically known as *Diascia barberae.*

The new cultivar is propagated from cuttings resulting from the cross of 'B15' and 'B139'. 'B15' is a deeprose flowering *Diascia* having. 'B15' is not commercially available and is not known by any synonyms. 'B139' is a pink flowering *Diascia*. 'B139' is not commercially available and is not known by any synonyms. Neither 'B15' nor 'B139' has been patented.

As a result of this cross the present cultivar was created in 2000 in Enkhuizen, Netherlands and has been repeatedly asexually reproduced by cuttings in Enkhuizen, Netherlands and Sarrians, France over a three-year period. It has been found to retain its distinctive characteristics through successive propagations, and this novelty appears to be firmly fixed.

The new *Diascia* plant is an annual in most climatical zones in the U.S., only in zones 7, 8, 9 and 10 it is a perennial plant.

DESCRIPTION OF THE DRAWING

This new *Diascia* plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new *Diascia*. The data which defines these characteristics were collected from asexual reproductions carried out in Enkhuizen, Netherlands. The plant history was taken on 10 weeks old plants, blossomed under natural light in a greenhouse.

Color readings were taken in the greenhouse under ambient light. Color references are primarily to The RHS Colour Chart of The Royal Horticultural Society of London.

TABLE 1

Differences between the new cultivar 'Diaspetis,' its parents and a similar cultivar

| | 'Diaspetis' | 'B15' | 'B139' | 'Rupert Lambert' |
|---|---|---|---|---|
| Flower color | Deepose | Deeprose | Pink | Deeprose |
| Plant size | Medium | Medium | Small | Small |
| Leaf size | Medium | Medium | Small | Small |
| Internodes | Short | Medium | Short | Long |

The Plant

Classification—Botanical: *Diascia barberae*
Parentage:
*Female parent.*—A seedling named 'B15' is one of our seedlings from our B-generation of plants bred in 1996.
*Pollen parent.*—A seedling named 'B139' is one of our seedlings from our B-generation of plants bred in 1996.
Growth habit: Compact, later spreading
Plant height: 14–23 cm
Spreading area of plant: 18–26 cm
Growth rate: Vigorous
Strength: Very good
Branching character: Freely branching and lateral branching at every node
Quantity of branches: 100–120 branches per plant
Blooming period: From April under November

The Stem

Diameter: 0.5–1.0 mm
Shape: Round
Color: 141B
Anthocyan pigmentation: Absent
Length of internode:
*Vegetative growth.*—10–20 mm.
*Generative growth.*—10–30 mm.
Pubescence: Not pubescent The Foliage Phyllotaxis: Opposite
Shape of blade: Cordate to ovate
Texture
*Upper side.*—Smooth.
*Lower side.*—Smooth.
Attachment to leaf: Petiolate
Venation: Pinnate
Leaf margin: Crenate
Leaf base: Subcordate
Leaf apex: Abruptly acute
Length: 13–18 mm
Width: 8–18 mm
Depth of incision: 1 mm
Color:
*Upper side.*—138A.
*Lower side.*—138B.
Pubescence: No pubescence
Length of petiole: 2–3 mm
Color of petiole: 138A
Petiole surface textile: Smooth The Bud Peduncle length: 25–25 mm, depending on season
Peduncle shape: Long and threadlike
Size of the bud
*Length.*—3 mm.
*Diameter.*—3 mm.
Shape: Oval
Color: 141A
Sepals:
*Color.*—141A.
*Form.*—Star-shaped.
*Number.*—5, parted.
*Size.*—1–2 mm.
*Shape.*—Elliptic, apex acute.
*Margin.*—Entire.
*Texture.*—Smooth.

The Flower

Flower width: 14–15 mm
Flower length: 14–18 mm
Flower depth: 6–8 mm
Flower aspect: Tipped upward and outward
Borne: Solitary
Form: Zygomorphic, five lobed, double nectar spur
Cluster: Raceme
Color:
*Upper surface.*—67D.
*Lower surface.*—68B.
Overlapping of the petals: Separate
Number of petals: Five
Shape of the petals: Two upper banner petals, two lateral petals and one larger basal lip petal. Base of two banner petals form a small yellow indentation (color yellow 9A) just above the reproductive organs. Center of two lateral petals form curved nectar spurs. Rounded lip petal is much larger and forms a nearly horizontal 'platform'
Petal margin: Entire
Petal surface texture: Smooth
Size of the banner petals:
*Length.*—3–5 mm.
*Width.*—4–7 mm.
Size of the lateral petals:
*Length.*—3–5 mm.
*Width.*—4–6 mm.
Size of the basal lip petal:
*Length.*—10–12 mm.
*Width.*—10–12 mm.
Spur:
*Length.*—8 mm.
*Color.*—Greyed purple 180B.
Number of flowers per raceme: 25–50.
Fragrance: No fragrance
Lastingness of the bloom: New florets continue to open in one raceme over a period of 18 days
Lastingness of one flower: About 5 days depending on temperature The Reproductive Organs Androecium:
*Stamen number.*—Three.
*Anther shape.*—Two-lobed.
*Anther size.*—Less than 1 mm.
*Anther color.*—Yellow 7A.
*Amount of pollen.*—Very much pollen.
*Pollen color.*—Yellow 7A.
Gynoecium:
*Pistil number.*—1.
*Stigma shape.*—Rounded.
*Pistil length.*—2–3 mm.
*Style color.*—Green 143A.
*Stigma color.*—Green white 157A.
*Ovary color.*—Green 134A.

The Seed

Seedset: No seedset has been observed

The Roots

Type of roots: Fibrous
Rooting habit: Fine and freely branching
Physiological and ecological characteristics: Good tolerance to heat and cold. Strong resistance to pests and diseases.

What is claimed is:

1. A new and distinct cultivar of *Diascia* plant named 'Diaspetis,' as substantially illustrated and described herein.

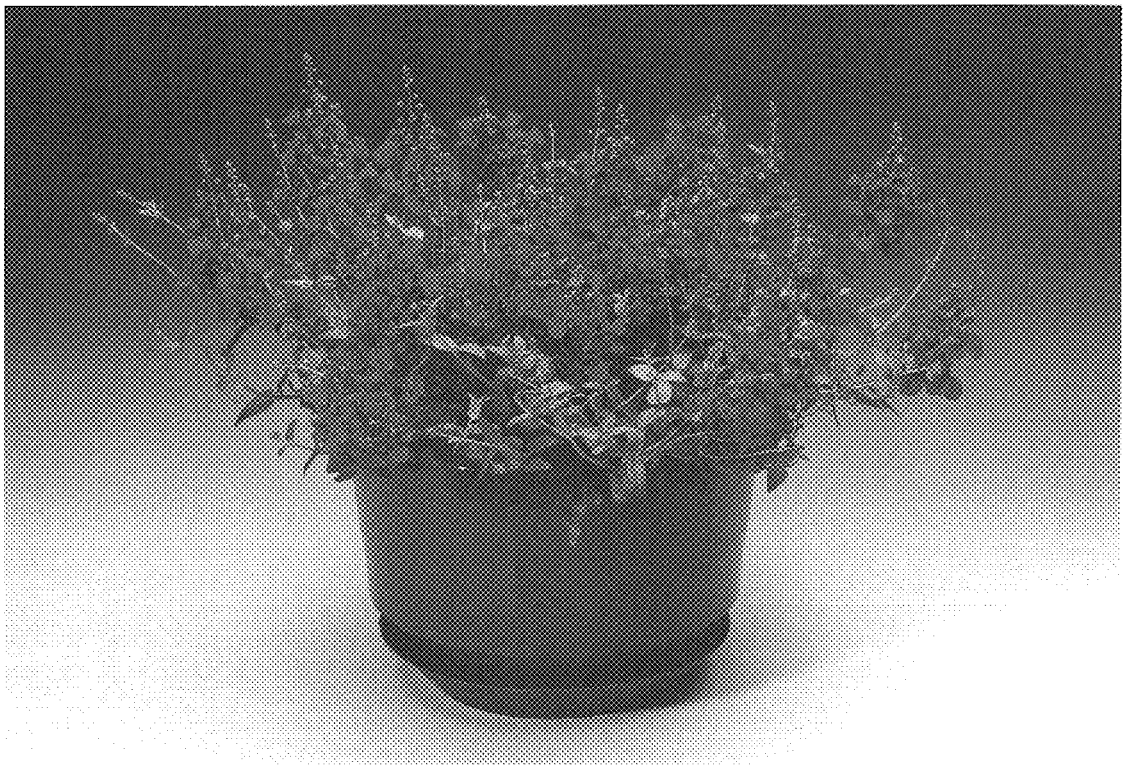

* * * * *